United States Patent
Higgins

(10) Patent No.: US 10,729,833 B2
(45) Date of Patent: Aug. 4, 2020

(54) INTRAVASCULAR PUMP WITH EXPANDABLE REGION AT LEAST PARTIALLY COLLAPSIBLE INTO RECESSES DEFINED BETWEEN IMPELLER BLADES

(71) Applicant: Cardiovascular Systems, Inc., St. Paul, MN (US)

(72) Inventor: Joseph P. Higgins, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 0 days.

(21) Appl. No.: 16/524,562

(22) Filed: Jul. 29, 2019

(65) Prior Publication Data
US 2020/0030511 A1   Jan. 30, 2020

Related U.S. Application Data

(60) Provisional application No. 62/711,748, filed on Jul. 30, 2018.

(51) Int. Cl.
*A61M 1/12* (2006.01)
*A61M 1/10* (2006.01)

(52) U.S. Cl.
CPC .......... *A61M 1/125* (2014.02); *A61M 1/1024* (2014.02); *A61M 1/122* (2014.02); *A61M 1/1008* (2014.02); *A61M 1/1029* (2014.02); *A61M 1/1086* (2013.01)

(58) Field of Classification Search
CPC .... A61M 1/125; A61M 1/122; A61M 1/1024; A61M 1/1008; A61M 1/1086; A61M 1/1029
See application file for complete search history.

(56) References Cited

U.S. PATENT DOCUMENTS

| | | | |
|---|---|---|---|
| 6,981,942 B2 | 1/2006 | Khaw et al. | |
| 10,350,341 B2* | 7/2019 | Throckmorton | .... A61M 1/1034 |
| 2008/0132747 A1 | 6/2008 | Shifflette | |
| 2011/0282128 A1 | 11/2011 | Reitan et al. | |
| 2013/0053623 A1 | 2/2013 | Evans et al. | |
| 2016/0287771 A1 | 10/2016 | Khanal et al. | |

OTHER PUBLICATIONS

International Search Report and Written Opinion, dated Oct. 21, 2019, for PCT Application No. PCT/US19/44063, filed Jul. 30, 2019.

* cited by examiner

*Primary Examiner* — Mark Bockelman
(74) *Attorney, Agent, or Firm* — Barnes & Thornburg LLP; Jeffrey R. Stone

(57) ABSTRACT

The present invention provides an intravascular blood pump comprising a housing that is at least partially expandable and collapsible and having an impeller with one or more blades attached thereto. The housing having spanning sections that are aligned with the blade(s) and adapted to collapse into recesses or spaces defined or provided between or along the blade(s) and along the central rotor to which the blade(s)s are attached.

20 Claims, 4 Drawing Sheets

INTRAVASCULAR PUMP WITH EXPANDABLE REGION AT LEAST PARTIALLY COLLAPSIBLE INTO RECESSES DEFINED BETWEEN IMPELLER BLADES

CROSS-REFERENCE TO RELATED APPLICATIONS

This application claims priority to U.S. Provisional Patent Application No. 62/711,748, filed Jul. 30, 2018 and titled INTRAVASCULAR PUMP WITH EXPANDABLE FRAME COLLAPSIBLE INTO BLADE RECESSES, the contents of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to an intravascular blood pump with an expandable and collapsible inlet region.

Description of the Related Art

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a flow inducer, known in the art as component that directs flow into the impeller from the inflow apertures or inlet; a rotational impeller; and a flow diffuser and/or outflow structure known in the art as functioning to straighten or redirecting the rotational flow created by the rotational impeller into axial flow; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the flow inducer 6 before being urged forward by the rotating impeller 8. The blood flow may then be modified by a flow diffuser 9 and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; and 8,992,163.

Known LVAD devices will typically comprise an angled housing to accommodate the aortic arch, the angle or bend generally in the range of 135 degrees.

LVAD devices with integrated motors within the housing must be small enough to allow atraumatic intravascular translation and positioning within the heart. Though various means are known to collapse portions of the device while within the catheter or delivery sheath, including the housing and/or the impeller or parts thereof such as the blades, the size of the collapsed device may be limited by the integrated motor.

In addition, the known LVAD devices comprise a delivery configuration wherein the housing and/or impeller, e.g., the blades on the impeller, may be reduced in diameter and, when delivered distally from the delivery catheter or sheath, the collapsed elements are enabled to expand. These devices are limited in several respects. First, the collapsing and expanding comprises at least a portion of the housing that is occupied by the impeller. Second, the inflow region of the housing, that is the region distal to the rotational impeller and the stationary inducer or flow straightener, comprises an area of opportunity to optimize blood flow through the cannula or housing. Known LVAD or VAD devices do not take advantage of this opportunity. Third, known LVAD or VAD devices comprise a flow inducer or flow straightener encountered by blood upon entry into the pump which can contribute to, inter alia, thrombosis and/or hemolysis. Fourth, reducing crossing profile of the VAD or LVAD device is critical for reasons discussed herein, a design requirement made more difficult by the need to extend electric leads across or along the housing of the device, wherein the electrical leads may be used for, e.g., powering and/or communicating with a motor or sensor(s) or other operational powered element. In this connection, electric leads require profile reduction to keep the crossing profile as low as possible, as well as insulation and/or spacing between adjacent leads where such insulation and/or spacing is necessary or desired. Further, a direct method to measure pressure and/or flow rate is desired.

Various embodiments of the present invention address these, inter alia, issues.

The figures and the detailed description which follow more particularly exemplify these and other embodiments of the invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 1:
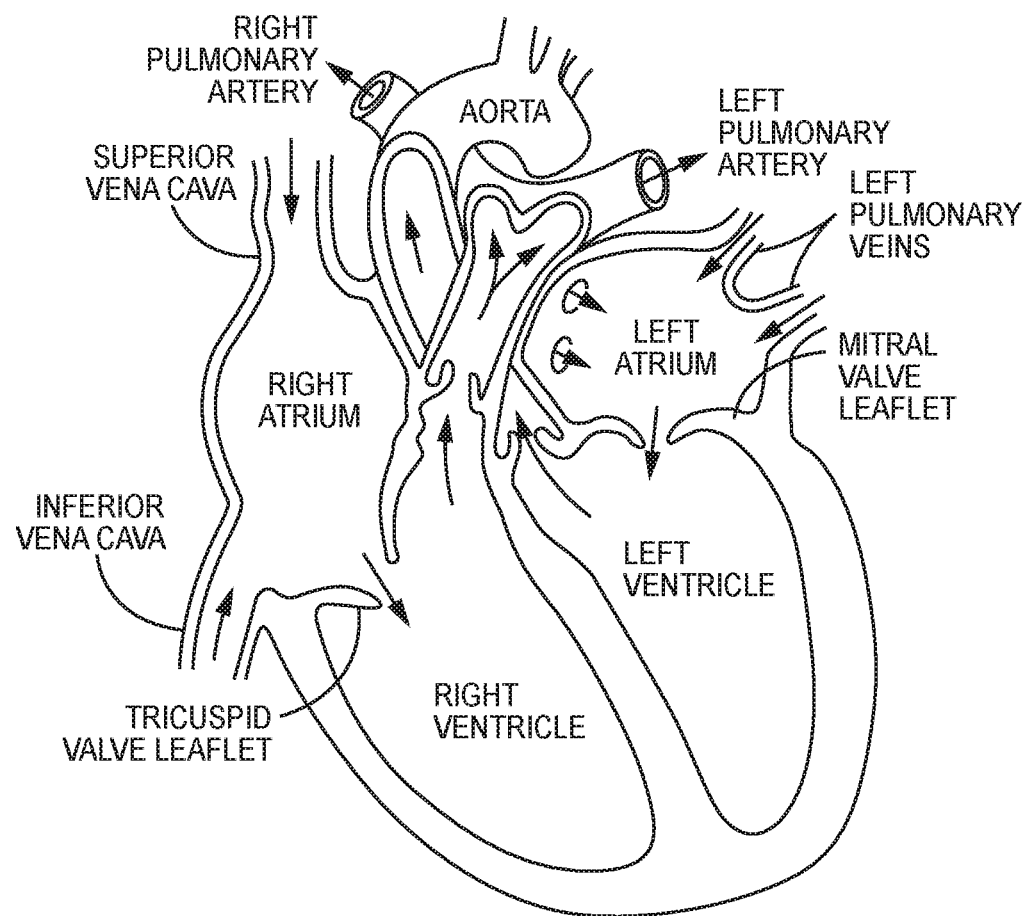
FIG. 1 is a cutaway view of the human heart.
Figure 2:
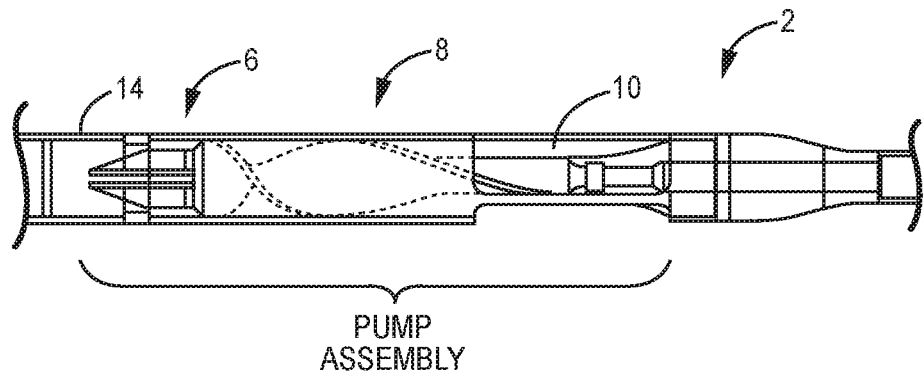
FIG. 2 is a cross-sectional view of a prior art device.
Figure 3:
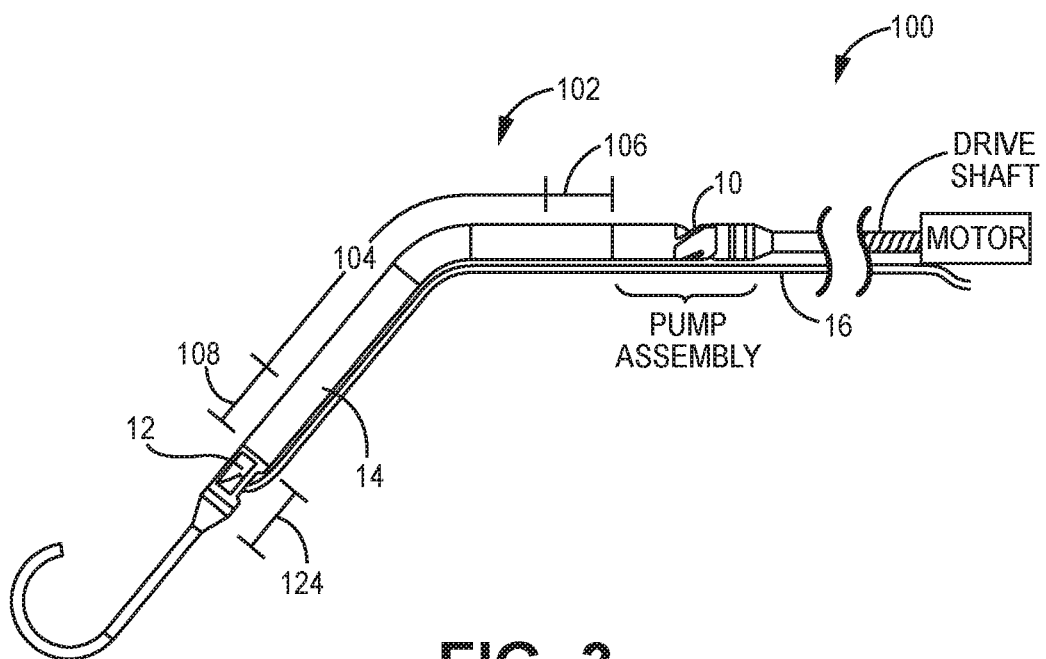
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device. The motor is shown as located on the proximal end of the device outside the patient's body and connected with a rotational drive shaft that is, in turn, connected with the impeller or rotor 8 or pump assembly. However, as is well known in the art, the motor may be located within the housing of the device itself, wherein the motor is typically mounted on the proximal side of the rotor 8 or impeller or pump assembly. Either of these configurations may be used together with various embodiments of the present invention as described herein.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller or rotor 8 or pump assembly. The configuration shown in FIG. 3 may comprise a delivery configuration with an expandable region 102 compressed within an introducer or delivery sheath or catheter 200.

With reference generally to the Figures, device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end and a distal end. The proximal end of the expandable region 102 abuts or is adjacent to a distal end of the proximal non-expandable region 122 while the distal end of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Alternatively, the housing H of device 100 in FIG. 3 may be non-expandable.

Figure 4:
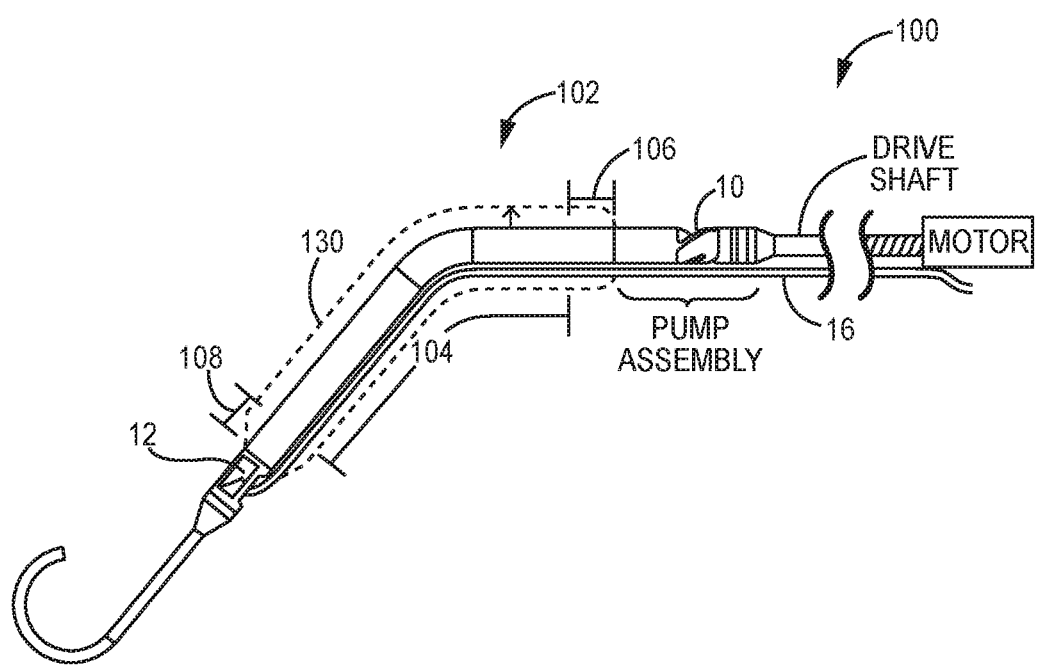
FIG. 4 is a side cutaway view of one embodiment of the present invention.

FIG. 4 illustrates an expandable embodiment of device 100 and in dashed lines the change in diameter to/from a collapsed, deformed expandable region to an exemplary expanded undeformed expandable region, extending distally from a point distal to the end of the impeller, rotor and/or pump assembly along the hollow cannula to a point just proximal of the inlet apertures. The expandable region 102 may expand to a maximum undeformed diameter within the range of 12-20 Fr, more preferably between 16-20 Fr. In contrast, the unexpanded region remains at a substantially fixed diameter within the range of 9 to 12 Fr.

With continued reference to FIGS. 3 and 4, and the remaining Figures generally, the device 100 may comprise an expandable region 102 that may be, either partially or completely, biased to the expanded configuration and, therefore, comprise a material or structure that facilitates expansion and may be biased to expand. Exemplary construction of the expandable region 102 may comprise a support structure 130 that is surrounded by an outer material, e.g., a jacket or coating or sleeve comprised of a plastic or polymeric material that accommodates an expansion of the underlying support structure as is known in the art. The support structure 130 may be formed of a shape memory material, for example Nitinol or similar. Other materials may comprise gold, tantalum, stainless steel, metal alloys, aerospace alloys and/or polymers including polymers that expand and contract upon exposure to relative heat and cold. In other cases, at least a portion of the expandable region 102, e.g., a central expandable section 104 discussed infra, may comprise a polymeric or other material sleeve that is configured to allow and/or accommodate expansion and collapsing and a support structure 130 may be omitted. FIG. 4 provides a rotational drive shaft connected with the impeller assembly and is, in turn, connected with a prime mover such as an electric motor that is located outside the patient's body. It will be understood, however, that the various embodiments of the inventions discussed herein may also be used in combination with blood pumps comprising motors integrated therein, i.e., no external motor. Further, as discussed above, device 100 may comprise an expandable housing H or region 102 or may be non-expandable.

In many of the embodiments described herein, the expandable region 102 may comprise a single expandable region, without need or reason to distinguish between a proximal transition section, central expandable section and/or distal transition section.

Generally, the expandable region 102 of the present invention may comprise a support structure 130 surrounded by a polymer coating or jacket that adapts to expansion and collapsing of the expandable region 102.

Further, the support structure 130 may comprise an expandable stent-like structure formed of a series of cells formed from interacting and/or interconnected wires and/or struts and that enable collapsing and biased expansion of a structure, e.g., a stent, as is known in the art. For example, see U.S. Pat. No. 5,776,183 to Kanesaka; U.S. Pat. No. 5,019,090 to Pinchuk; U.S. Pat. No. 5,161,547 to Tower; U.S. Pat. No. 4,950,227 to Savin; U.S. Pat. No. 5,314,472 to Fontaine; U.S. Pat. Nos. 4,886,062 and 4,969,458 to Wiktor; and U.S. Pat. No. 4,856,516 to Hillstead, the disclosures of each of which are hereby incorporated in their entirety by reference.

The expandable region 102 described herein is merely exemplary and not limiting in any regard. As such, any expandable housing H of a blood pump device 100 is readily adaptable to the various embodiments of the present invention relating to insulation and/or spacing and/or profile reduction or integration of electrical leads or conductors E within or along the blood pump housing. Expandable region 102 may also comprise a single region capable of expansion and collapse.

Figure 5:
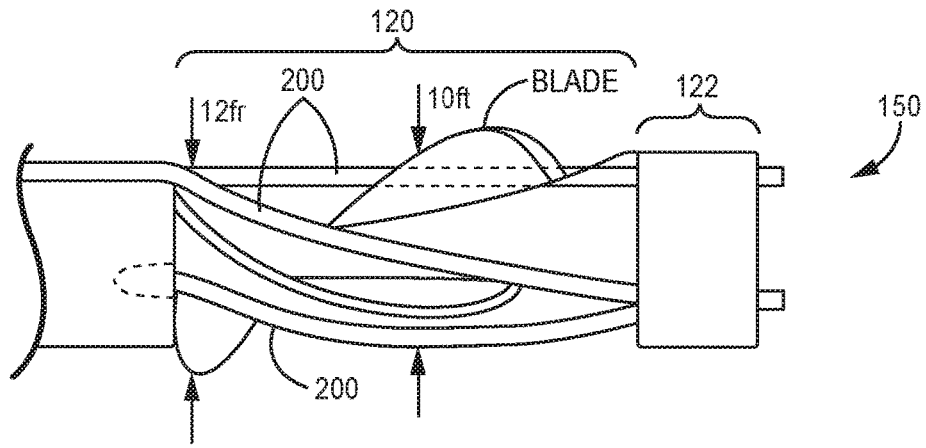
FIG. 5 is a side cutaway of one embodiment of the present invention.
Figure 6:
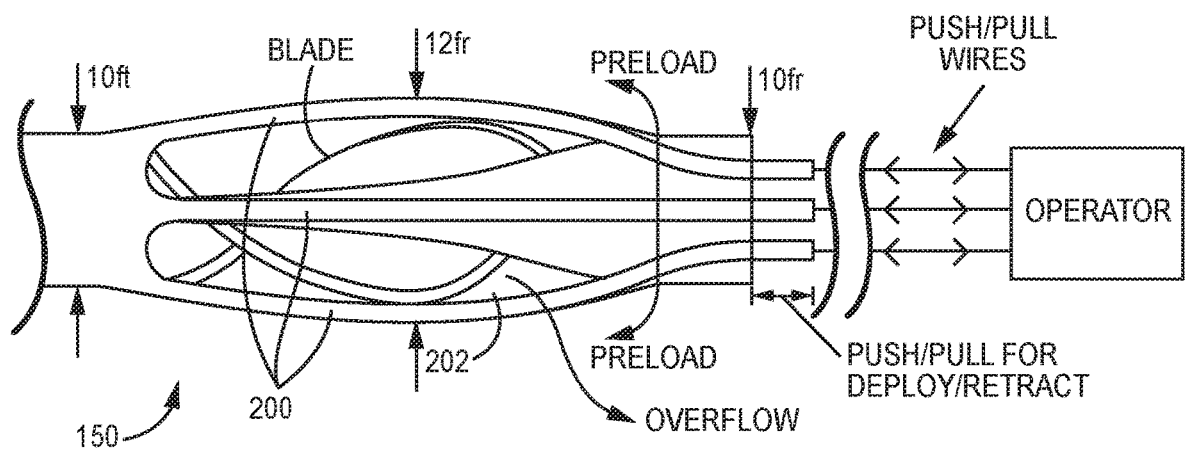
FIG. 6 is a side cutaway of one embodiment of the present invention.
Figure 7:
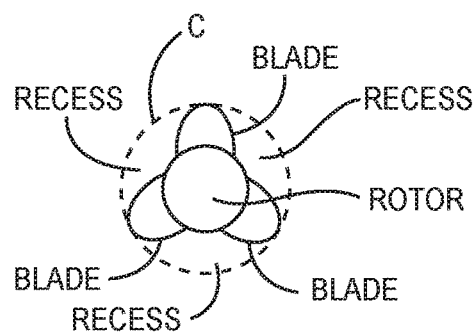
FIG. 7 is an end cross-sectional view of one embodiment of the present invention.

Turning now to FIGS. 5-7, and with continuing reference to FIGS. 1-4, the device 150 may comprise an expandable region 102 that may be located distal to the impeller or rotor or pump assembly 120, wherein impeller assembly 120 comprises a housing that further comprises spanning sections 200 that connect a proximal non-expandable area 122, located just proximal to the impeller assembly 120 and the housing portion located distal to the impeller assembly 120. The housing portion just distal to the impeller assembly 120 may be part of the expandable region 102. A single region of expansion and collapsing may comprise the housing region at least partially surrounding the impeller assembly 120.

As shown, impeller assembly 120 comprises a central rotor with blades defined therealong in spaced apart configuration. There may be a single blade that spirals around the central rotor or impeller hub with a resulting spiraling blade recess therealong, or there may be more than one blade. FIG. 7 provides an end cutaway view of the impeller assembly 120, three blade protrusions extending radially away from the central rotor are shown. The space between each blade protrusion, as in FIG. 7, is defined as a recess with reduced outer diameter or outer circumference relative to the maximum outer diameter of impeller assembly measured by the outer diameter of opposing blade tips, or outer circumference comprising a circle C having a diameter, that connects the outer edges of each blade tip of FIG. 7, along the rotor.

Each spanning section 200 is a relatively narrow connector as shown and, thereby, defines outflow apertures 202 that allow the blood to be expelled therethrough. The spanning sections 200 of the present invention are spaced rotationally around the housing so that when the impeller assembly 120 is not rotating, each spanning section 200 may align with, and within, one of the recesses between the blades.

Spanning sections 200 may, in certain embodiments, be relatively flexible and adapted to be manipulated by an operator using push/pull wire(s) attached to the spanning sections 200 as shown in FIG. 6. When the impeller assembly 120 is not rotating and requires a low profile in a collapsed configuration with a small diameter, for example during advancement and/or retraction into the patient's vasculature, the operator may pull the wires proximally to enable the spanning sections 200 to move into an associated recess between the blade protrusions. When an expanded or working configuration is required, the operator may push the push/pull wire(s) to cause spanning sections 200 to expand out of the recess areas radially a distance sufficient to allow the impeller to spin without obstruction by the spanning sections 200.

Spanning sections 200 may be alternatively formed with a biased collapsed configuration. In this embodiment, the spanning sections 200 may comprise a shape memory material that provides a biased position for each spanning section 200 in the lower radial position, i.e., disposed to be biasingly located within the recesses of the impeller assembly defined between the blade protrusions thereof unless a force overcoming the bias is applied to the spanning sections 200. Thus, pushing a push wire (no pull wire force is required in this case due to the biasing forces) in the distal direction may force the spanning sections 200 radially out of the default or biased position within the blade recesses and radially outward to allow the impeller to spin without interference.

Still more alternatively, spanning sections 200 may be formed with a biased expanded location that, when achieved, will not interfere with the rotation of the impeller. In this embodiment, only a pull wire will be required to overcome the prevailing bias of the spanning sections 200 to move them radially inward to a position within the blade recesses, wherein the spanning sections 200 will interfere with the rotation of the impeller blade(s). Further, in certain embodiments of this embodiment, spanning sections 200 may be deformed to a position that is located within the recesses between blade protrusions to achieve the lowest profile possible to accommodate delivery. The deformed position within the recesses may be achieved by removably fixing the spanning sections 200 within the recesses. For example, an adhesive or other material that dissolves on contact with blood may be used. Suture(s) may be used that may also dissolve on contact with blood and/or may be broken by rotating the impeller blade slightly. A collar wrapping around the impeller's central rotor and the spanning sections may also be employed to achieve and maintain the deformed position of the spanning sections within the recesses between the blade protrusions, wherein the collar comprises a material that may be easily broken by slightly rotating the impeller and/or that may dissolve on contact with blood.

The result of the present invention is a lower profile in a collapsed configuration for the region of the device at the impeller assembly. In the case wherein the blade protrusions or blades are rigid and not collapsible, the maximum outer diameter is dictated by the outer edges of the blades. Collapsible blades or blade protrusions allow a still-further reduced collapsed configuration. This enables easier delivery of the device through the introducer sheath or delivery catheter and works in combination with the expandable region 102 to move between a lower profile, smaller diameter collapsed or delivery configuration and a higher profile and larger diameter expanded or working configuration.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A blood pump having a housing and comprising:
   an impeller assembly comprising a central rotor and at least one blade disposed therealong and defining at least one blade recess defined along the central rotor, the impeller assembly operationally connected with a rotational motor adapted to rotate the impeller assembly;
   the blood pump housing comprising a collapsible and expandable region comprising two or more spanning sections disposed at least partially over the impeller assembly,
   wherein each spanning section is configured to align with and collapse into, and expand out of, one of the at least one blade recesses.

2. The blood pump of claim 1, further comprising a push and/or pull wire operatively connected with each spanning section, wherein the push and/or pull wire is adapted to move each spanning section to an expanded configuration and a position that does not interfere with the rotation of the impeller.

3. The blood pump of claim 2, wherein pulling the push and/or pull wire moves the two or more spanning sections to a collapsed position within the blade recess that will interfere with the rotation of the impeller.

4. The blood pump of claim 1, wherein each of the two or more spanning sections are biased to collapse to a position within one of the at least one blade recesses.

5. The blood pump of claim 4, further comprising a push and/or pull wire operatively connected with each spanning section and adapted to move each of the two or more spanning sections radially outward from the biased position to a position that will not interfere with the rotation of the blades.

6. The blood pump of claim 1, wherein the two or more spanning sections are biased to take an expanded position that will not interfere with the rotation of the impeller.

7. The blood pump of claim 6, further comprising a push and/or pull wire operatively connected with each of the two or more spanning sections and adapted to move each of the spanning sections radially inward from the biased position to a collapsed position that will interfere with the rotation of the impeller.

8. The blood pump of claim 1, wherein the two or more spanning sections comprise a shape memory material.

9. The blood pump of claim 8, wherein the shape memory material comprises a metal and/or a polymer.

10. The blood pump of claim 1, wherein the at least one blade spirals around the central rotor.

11. The blood pump of claim 10, wherein the at least one blade recess spirals around the central rotor.

12. The blood pump of claim 1, wherein the at least one blade recess spirals around the central rotor.

13. The blood pump of claim 12, wherein the at two or more spanning sections are configured to collapse into, and expand out of, the at least one blade recess.

14. A blood pump having a housing and comprising:
    an impeller assembly comprising a central rotor and at least one blade disposed therealong and defining at least one blade recess defined along the central rotor, the impeller assembly operatively connected with a rotational motor configured to rotate the impeller assembly;
    the blood pump housing comprising a collapsible and expandable region comprising two or more spanning sections disposed at least partially over the impeller assembly,
    wherein each spanning section is configured to align with and collapse into, and expand out of, one of the at least one blade recesses,
    wherein each of the two or more spanning sections are biased to collapse to a position within one of the at least one blade recesses.

15. The blood pump of claim 14, wherein the two or more spanning sections comprise a shape memory material.

16. The blood pump of claim 15, wherein the shape memory material comprises a metal and/or a polymer.

17. The blood pump of claim 14, wherein the at least one blade spirals around the central rotor.

18. The blood pump of claim 17, wherein the at least one blade recess spirals around the central rotor.

19. The blood pump of claim 14, wherein the at least one blade recess spirals around the central rotor.

20. The blood pump of claim 14, further comprising a push and/or pull wire operatively connected with each of the two or more spanning sections and configured to expand the collapsed spanning sections to a position that does not interfere with rotation of the at least one blade.

* * * * *